United States Patent [19]

Champion et al.

[11] Patent Number: 5,266,553
[45] Date of Patent: Nov. 30, 1993

[54] METHOD OF MANUFACTURING A DRY WATER-SOLUBLE HERBICIDAL SALT COMPOSITION

[75] Inventors: James K. Champion, Palos Park, Ill.; Conrad T. Harwell, Lowell, Ind.

[73] Assignee: Riverdale Chemical Company, Glenwood, Ill.

[21] Appl. No.: 779,896

[22] Filed: Oct. 21, 1991

[51] Int. Cl.$^5$ .................... A01N 25/12; A01N 37/10; A01N 57/04; A01N 43/72
[52] U.S. Cl. ........................... 504/206; 504/222; 504/260; 504/284; 504/297; 504/298; 504/320; 504/321; 504/323; 504/324; 504/325; 71/DIG. 1
[58] Field of Search .................... 71/117, DIG. 1; 504/323, 324, 206, 222, 260, 284, 297, 298, 320, 321, 325

[56] References Cited

U.S. PATENT DOCUMENTS

| | | | |
|---|---|---|---|
| 2,522,488 | 9/1950 | Bersworth | 71/117 |
| 2,694,625 | 11/1954 | Warren | 71/117 |
| 3,023,096 | 2/1962 | Guth | 71/2.4 |
| 3,103,432 | 9/1963 | Guth | 71/2.4 |
| 3,208,843 | 9/1965 | Guth | 71/2.6 |
| 3,940,260 | 2/1976 | Kauffman | 71/110 |

OTHER PUBLICATIONS

Product Label–"2,4-D Dri-Amine", Uniroyal Chemical, Elmira, Ont. 1978.
Product Information–"SAVAGE TM", Platte Chemical Co., Fremont, NB. 1991.
Pavia et al., *Introduction to Organic Laboratory Techniques* W. B. Saunders Co.; Philadelphia, pp. 494-496, 505-516, 1984.

*Primary Examiner*—Glennon H. Hollrah
*Assistant Examiner*—S. Mark Clardy
*Attorney, Agent, or Firm*—Marshall, O'Toole, Gerstein, Murray & Borun

[57] ABSTRACT

A method of manufacturing a solid, water-soluble herbicidal composition comprising a water-soluble salt of a herbicidal compound is disclosed. The herbicidal compound is a water-insoluble compound that includes a carboxylic acid functionality, such as a phenoxy-substituted carboxylic acid compound or a substituted benzoic acid compound, and is sufficiently pure to form a dry, solid herbicidal salt composition after interaction with a suitable neutralizing base, such as ammonia, an alkylamine, a dialkylamine, a trialkylamine, a hydroxyalkylamine, a dihydroxyalkylamine, an alkaline salt of an alkali metal or a combination thereof. The dry herbicidal salt composition includes at least about 90% by weight of the water-soluble herbicidal salt, and dissolves rapidly and essentially completely in water to form an aqueous herbicidal solution including up to about 75% by weight of the water-soluble herbicidal salt.

15 Claims, No Drawings

5,266,553

METHOD OF MANUFACTURING A DRY WATER-SOLUBLE HERBICIDAL SALT COMPOSITION

FIELD OF THE INVENTION

The present invention relates to a solid, water-soluble herbicidal salt composition and its method of manufacture. More particularly, the present invention relates to a method of manufacturing a dry herbicidal salt composition, preferably in the form of a powder, comprising a water-soluble salt of an herbicidal compound, wherein the herbicidal compound includes a carboxylic acid functionality, like a substituted benzoic acid herbicide, such as 2-methoxy3,6-dichlorobenzoic acid, or a phenoxy-substituted carboxylic acid herbicide, such as 2,4-dichlorophenoxyacetic acid, or wherein the herbicidal compound is bentazon; and wherein the herbicidal compound is sufficiently pure such that discrete dry particles of the water-soluble herbicidal salt composition are formed after interaction with a suitable neutralizing base, like dimethylamine, diethanolamine, potassium hydroxide or ammonia. The solid particles of the water-soluble herbicidal salt composition are dry to the feel; include at least about 90%, and usually at least about 95%, and up to about 99.5%, by weight of the water-soluble herbicidal salt; and dissolve rapidly and essentially completely, in either cold or warm, or hard or soft water, to form an aqueous herbicidal solution including up to about 75% by weight of the water-soluble herbicidal salt.

BACKGROUND OF THE INVENTION

It is known that certain compounds, like substituted benzoic acid herbicides and phenoxy-substituted carboxylic acid herbicides, possess selective herbicidal activity against broadleaf vegetation at dosages as low as a few ounces of active herbicide per acre. The substituted benzoic acid and the phenoxy-substituted carboxylic acid herbicides have been applied to susceptible vegetation in their acid form, but herbicidal effectiveness was poor because the water-insoluble acid form these herbicides did not sufficiently penetrate the leaves of susceptible vegetation for fast and efficient eradication.

Therefore, the substituted benzoic acid herbicides and the phenoxy-substituted carboxylic acid herbicides, and other herbicidal compounds including a carboxylic acid functionality, traditionally were converted from the acid form to an ester form or to a salt form to enhance water solubility and leaf penetration properties. Both the ester forms and the salt forms of these herbicidal compounds are available commercially and are provided as liquid products including a known, but variable, amount of the active herbicide. A predetermined amount of water then is added to dilute the active herbicide before spraying the susceptible vegetation. The predetermined amount of water is related to the concentration of the active herbicide in the liquid herbicidal product and the desired strength of the spraying solution.

In general, the ester forms of these herbicides are provided as petroleum distillate-based emulsifiable concentrates that are diluted with water. The resulting herbicide emulsion then is sprayed on the vegetation to be controlled. The salt forms of these herbicides are provided as concentrated aqueous solutions that are diluted with water. Then the resulting aqueous herbicidal solution is sprayed on the vegetation to be controlled. For reasons of economy and safety to the environment and the herbicide applicator, the aqueous-based salt form of the herbicide often is the preferred form of the herbicide. As will be discussed more fully hereinafter, some solid forms of these herbicidal compounds also are available.

In particular, the ammonium salt, various alkylamine and alkanolamine salts, and the alkali metal salts of the substituted benzoic acid herbicides and the phenoxy-substituted carboxylic acid herbicides, and other herbicidal compounds including a carboxylic acid functionality, have been used as selective herbicides for controlling a wide range of broadleaf weed species, particularly in cereal crops, in gardens and in turf maintenance. These herbicidal compounds have been provided in a salt form as concentrated aqueous solutions, in an ester form as concentrated solutions of a petroleum distillate-based solvent or in the form of solid granules including an inert, and usually water insoluble, support material incorporating an acid, ester or salt form of the herbicidal compound. Both the liquid and granular herbicidal compositions can include a single herbicide or a mixture of herbicides, depending upon the herbicide combination best suited to control a particular weed species.

The concentrated, aqueous herbicidal salt solutions are supplied to the consumer, or applicator, in plastic or metal containers. The applicator charges a measured amount of the herbicidal salt solution into a mixing vessel or tank, then the concentrated herbicidal salt solution is diluted to the desired concentration by adding sufficient water to the mixing vessel or tank. The diluted herbicidal salt solution then is sprayed onto the crop, or onto the turf, at the appropriate dosage rate.

The amount of active herbicidal salt present in the concentrated aqueous herbicidal salt solution is limited by the water solubility of the specific salt of a particular herbicide. The amount of active herbicide, as a salt, in the aqueous solution therefore is limited to a maximum of about 85% by weight of the solution. However, several salts of several different substituted benzoic acid herbicides and phenoxy-substituted carboxylic acid herbicides have demonstrated a much lower solubility in water.

Therefore, the formulation of substituted benzoic acid herbicides or phenoxy-substituted carboxylic acid herbicides, and of other herbicidal compounds including a carboxylic acid functionality, into aqueous, or petroleum distillate-based, liquid concentrates has demonstrated several disadvantages. The petroleum distillate-based liquid concentrates have the disadvantage of being expensive and combustible, and of possessing sufficient volatility to harm beneficial nearby vegetation, in addition to presenting additional health and environmental concerns beyond those posed by the herbicidal compound itself. Furthermore, both the petroleum distillate-based and the aqueous concentrates include a significant amount of solvent that adds to the size, weight and cost of containers, transportation and handling In addition, the disposal of empty herbicide containers results in potential hazards to the environment because of possible ground contamination by any residual herbicide remaining in the container, and by the non-biodegradability of the herbicide container itself.

Many of these disadvantages are not overcome by using a granular form of the herbicidal compound, wherein the herbicidal compound is impregnated into or absorbed onto an inert support. In the granular form, the herbicide product is supplied in a plastic bag, a plastic drum or a fiber keg. The granular herbicide product is applied to vegetation by directly spreading the herbicide granules onto the vegetation at a suitable dosage rate. The granular herbicide products generally have an active herbicide content in the range of from about 0.5% to about 50% by weight. Similar to the liquid herbicidal concentrates, the volume and weight of the inert support material increase the size and cost of the container, and the costs of transportation and handling, of the granular herbicide product. In addition, the disposal of empty herbicide containers poses the same adverse environmental concerns as discussed above in regard to the concentrated liquid herbicide products.

Therefore, it would be advantageous to provide a highly-concentrated herbicidal composition, in the form of a solid, and preferably a powder, that can be added to water at the application site, and that dissolves quickly and essentially completely, in hard or soft water, to provide an aqueous solution of the herbicidal compound that can be applied directly to the crop or to the turf, or that can be diluted further as necessary. Such a highly-concentrated, solid herbicidal composition reduces container, shipping and handling costs. More importantly, and as will be discussed more fully hereinafter, if the highly-concentrated, solid herbicidal composition is sufficiently dry, such as including less than 3%, and preferably less than 1%, water, the herbicidal composition then can be supplied in water-soluble packets. Water-soluble packets including a water-soluble herbicidal composition would eliminate direct contact between the applicator and the herbicidal composition, such as occurs during dilution of a concentrated liquid herbicidal composition, and would eliminate the need to dispose of an empty herbicide container. Accordingly, safety to the applicator and safety to the environment are enhanced.

As previously stated, water-soluble forms of substituted benzoic acid herbicides, phenoxy-substituted carboxylic acid herbicides, other herbicidal compounds including a carboxylic acid functionality and bentazon are known. Specifically, the lithium, sodium and potassium salts of 2,4-dichlorophenoxyacetic acid (2,4-D) and related phenoxy herbicides have ben reported in the literature and in patents, and have been marketed. For example, Morrill U.S. Pat. No. 2,519,780 discloses aqueous solutions of alkali metal, ammonium and alkylammonium salts of 2,4-D that further include an ethoxylated fatty acid to help prevent the precipitation of the 2,4-D salt in hard water. Other patents disclosing aqueous solutions of substituted benzoic acid or phenoxy-substituted carboxylic acid herbicides include: U.S. Patent Nos. 2,522,488; 2,606,876; 2,694,625; 2,992,913; 3,081,162; 3,103,432; 3,248,208; 3,284,186; and 4,123,253. Granular herbicidal compositions including an herbicide impregnated into or absorbed onto an inert support are disclosed for example in Kenney, Jr. et al. U.S. Pat. No. 2,695,839; Wright U.S. Patent No. 2,792,295; Galloway U.S. Patent Nos. 3,056,723 and 3,168,437; Ordas U.S. Patent No. 3,421,882; Hokama U.S. Pat. Nos. 3,870,732, 3,910,974, 4,022,610; and Poignant et al. U.S. Pat. No. 4,013,451.

As previously indicated, the substituted benzoic acid herbicides and the phenoxy-substituted carboxylic acid herbicides generally are manufactured, and marketed, as liquid concentrates or as granules including an inert support. However, some dry salts of these and other herbicidal compounds also have been disclosed and marketed. For example, Richter, in U.S. Pat. No. 3,012,870, discloses the preparation of the sodium, ammonium, dimethylammonium and other salts of 2-methoxy-3,5-dichlorobenzoic acid in an organic solvent. The salts disclosed by Richter then were admixed with an inert support and applied as a dust. Guth, in U.S. Pat. No. 3,023,096, discloses the manufacture of potassium and lithium 2,4-dichlorophenoxyacetate. The lithium salt of 2,4-D is available commercially, under the commercial tradename, LITHATE, from Guth Corporation, Naperville, Ill., as a 95% active lithium 2,4-D composition. Other patents disclosing the preparation, or use, of solid phenoxy or benzoic acid herbicidal salts include Guth, U.S. Pat. Nos. 3,103,432 and 3,208,843; and Kauffman, U.S. Pat. No. 3,940,260.

The lithium salt of 2,4-D is a stable, dry compound and is highly water-soluble. However, the lithium salt of 2,4-D also possesses several disadvantages. For example, lithium is expensive, and lithium can accumulate to toxic levels in the soil. Furthermore, the lithium salt of 2,4-D is a slow acting herbicidal salt compared to other salts of 2,4-D, like the dimethylamine salt. Therefore, it would be advantageous to provide a dry, highly-concentrated salt of an herbicidal compound that includes a carboxylic acid functionality, like a phenoxy-substituted carboxylic acid herbicide salt or a substituted benzoic acid herbicide salt, that does not possess the disadvantages of the lithium salt. It is known that the ammonium, the alkylamine and the alkanolamine salts of 2,4-D and related phenoxy herbicides overcome the disadvantages presented by the lithium salt, but such salts have been difficult to prepare as dry herbicidal salt compositions including at least 90% by weight of the active herbicidal salt. As will be demonstrated more fully hereinafter, the method of the present invention provides such dry and highly-active herbicidal salt compositions.

A solid form of the dimethylamine salt of 2,4-D also is available commercially from Platte Chemical Co., Fremont, NB., under the brand name SAVAGE. This product includes 95% by weight of the dimethylamine salt of 2,4-D and is water soluble. This product has a pH of approximately 9 and has a "fishy" amine-like odor, thereby indicating that SAVAGE includes an excess amount of dimethylamine to ensure complete water solubility of the product. The presence of excess amine however provides a solid herbicidal composition, and solutions derived therefrom, that have an offensive odor and that are generally unpleasant to use. As will be demonstrated more fully hereinafter, the method of the present invention provides an herbicidal salt composition that does no include excess amine, and can be deficient in amine, and that is still completely water soluble. The elimination of excess amine, while maintaining complete water solubility, is surprising and new in the art. The elimination of excess amine also avoids the unpleasant odor from the composition and provides herbicidal solutions having an essentially neutral pH of about 5 to about 7, thereby overcoming the potentially corrosive properties of an herbicidal solution having a high alkaline pH.

SUMMARY OF THE INVENTION

The present invention is directed to a method of manufacturing a solid, water-soluble herbicidal salt composition comprising a water-soluble salt of an herbicidal compound that includes a carboxylic acid functionality, such as a water-soluble salt of a substituted benzoic acid herbicide or a water-soluble salt of a phenoxy-substituted carboxylic acid herbicide; bentazon; or a combination thereof. The water-soluble herbicidal salt composition includes at least 90%, usually at least 95%, and up to about 99.5% by weight of ammonium, an alkylammonium, a hydroxyalkylammonium or an alkali metal salt of a herbicidal compound that includes a carboxylic acid functionality, bentazon or a combination of such herbicidal compounds. Furthermore, the herbicidal salt composition is essentially completely soluble in water to form an aqueous herbicidal solution including up to about 75% by weight of the herbicidal salt.

Although the alkali metal salts of the substituted benzoic acid herbicides and the phenoxy-substituted carboxylic acid herbicides have been prepared and used in the solid form, it is both new and unexpected to provide the ammonium, alkylammonium and hydroxyalkylammonium salts of these herbicides, and other herbicidal compounds including a carboxylic acid functionality, as a dry, solid herbicidal salt composition. The alkali metal salts of the substituted benzoic acid and phenoxy-substituted carboxylic acid herbicides possess many properties of an inorganic salt, in that alkali metal salts of these herbicidal compounds can be prepared by neutralization with a suitable base, then dried, to yield particles of solid herbicidal salt composition. However, the ammonium, alkylammonium and hydroxyalkylammonium salts of these herbicidal compounds, although readily formed in solution, have proved difficult to crystallize, and to dry, to form solid particles including at least 90% by weight of the herbicidal salt.

In particular, the present invention is directed to a method of manufacturing a water-soluble ammonium, alkylammonium, hydroxyalkylammonium or alkali metal salt of an herbicidal compound including a carboxylic acid functionality or of bentazon. More particularly, the present invention provides a method of manufacturing a dry, water-soluble herbicidal salt composition including at least 90%, usually at least 95%, and up to about 99.5% by weight of the herbicidal salt. The herbicidal salt composition is essentially completely soluble in cold or warm water, or in hard or soft water, to provide an aqueous herbicidal solution including up to about 75% by weight of the herbicidal salt. The present invention is particularly useful in the manufacture of water-soluble herbicidal salt compositions of bentazon; a substituted benzoic acid herbicide, and especially methoxy-substituted or halogen-substituted benzoic acid herbicides; and of a phenoxy-substituted carboxylic acid herbicide, and especially chlorophenoxy-substituted carboxylic acid herbicides.

More particularly, the present invention is directed to the manufacture of a dry, powdered water-soluble herbicidal salt composition including a salt of bentazon or salt of a substituted benzoic acid herbicide or a salt of a phenoxy-substituted carboxylic acid herbicide. The water-soluble herbicidal salt can be an alkali metal salt, such as the potassium or sodium salt; or can be the ammonium salt. The water-soluble herbicidal salt also can be an hydroxyalkylammonium salt or a dihydroxyalkylammonium salt, such as the diethanolamine salt. To achieve the full advantage of the present invention, the water-soluble herbicidal salt is an alkylammonium salt, a dialkylammonium salt or a trialkylammonium salt, wherein the alkyl groups include from one to about four carbon atoms, like the dimethylammonium, ethylammonium, triethylammonium or isopropylammonium salt. The herbicidal compound can be bentazon; or can be a substituted benzoic acid herbicide, like 2,3,6-trichlorobenzoic acid or 2-methoxy-3,6-dichlorobenzoic acid; or can be a phenoxy-substituted carboxylic acid herbicide like 2,4.dichlorophenoxyacetic acid (2,4-D), 2-(2,4-dichlorophenoxy)propionic acid (2,4-DP), 2,4-dichlorophenoxybutyric acid (2,4-DB), 2-methyl-4-chlorophenoxyacetic acid (MCPA), 2-(2-methyl-4-chlorophenoxy)propionic acid (MCPP) or 2-methyl4-chlorophenoxybutyric acid (MCPB); or mixtures thereof. A dry, water-soluble herbicidal salt composition including other herbicidal compounds having a carboxylic acid functionality, like endothall, glufosinate, glyphosate or picloram, also can be manufactured by the method of the present invention.

In accordance with an important aspect of the present invention, it has been found that the purity of the herbicidal compound including the carboxylic acid functionality, and especially of the phenoxy. substituted carboxylic acid herbicides, is directly related to providing a dry, water-soluble herbicide salt composition, especially if the salt is an alkylammonium, a dialkylammonium, a trialkylammonium, a hydroxyalkylammonium, a di(hydroxyalkyl)ammonium or ammonium salt of the herbicidal compound. Such alkylammonium, hydroxyalkylammonium and ammonium herbicidal salts often do not solidify into a dry, particulate solid from an aqueous solution, but tend to form into sticky or wet, intractable, amorphous masses. However, it has been found that if the acid form of the herbicidal compound is of sufficient purity, such as including about 7% or less by weight of total impurities, then the corresponding alkylammonium, hydroxyalkylammonium or ammonium herbicidal salts can be obtained as a dry solid, such as a powder, including at least 90%, and usually at least 95%, and up to about 99.5% by weight of the water-soluble herbicidal salt.

In accordance with another important aspect of the present invention, the dry, water-soluble herbicidal salt composition first is formed in, and then isolated from, a solvent comprising water as the major component. To achieve the full advantage of the present invention, the solvent consists essentially of water, such as at least about 95% by weight water.

The dry water-soluble herbicidal salt composition is not prepared by a precipitation or crystallization, but is prepared by a method wherein the solvent, e.g., water, is separated from the herbicidal salt composition by evaporation under controlled conditions. As will be demonstrated more fully hereinafter, the herbicidal salt composition prepared by the method of the present invention demonstrates superior physical and esthetic properties compared to prior art dry, water-soluble herbicidal compositions. In addition, it is unnecessary to include organic solvents, like an alcohol or an ether, in the aqueous solvent either during the preparation of the herbicidal salt composition or during the separation of the herbicidal salt composition from the water. Furthermore, the herbicidal salt composition recovered from the water does not require rinsing with an organic solvent, or a solubilizing/reprecipitating procedure, to provide dry solid particles of the herbicidal salt composition.

The present method also provides an herbicidal salt composition that is essentially completely soluble in water. Previous attempts to prepare a dry and completely water-soluble ammonium, an alkylammonium or a hydroxyalkylammonium salt of bentazon or of an herbicidal compound including a carboxylic acid functionality have failed not only with respect to providing a dry and easy-to-handle solid product, but also with respect to complete water solubility of the solid herbicidal salt composition. Previous methods of removing the aqueous solvent from an ammonia, an alkylammonium or a hydroxyalkylammonium herbicidal salt also stripped a portion of the ammonia, the alkylamine or the hydroxyalkylamine used to neutralize the acid form of the herbicidal compound. Accordingly, a portion of the herbicidal salt was reconverted to the acid form of the herbicidal compound. The acid form of the herbicidal compound generally is water insoluble, and accordingly, if a sufficient amount of the acid form of herbicidal compound is present, then the herbicidal salt composition is not completely soluble in water. Therefore, previous methods included an excess amount of the neutralizing base in the herbicidal composition. This excess amount of neutralizing base provided a composition that had a high pH and possibly was corrosive; and in the case of an amine neutralizing base, a composition that had an offensive "fishy" odor. Surprisingly, the present method overcomes the loss of ammonia, alkylamine or hydroxyalkylamine during the step of removing the aqueous solvent from the herbicidal salt to provide an essentially completely water-soluble herbicidal salt composition including at least 90%, usually at least 95%, and up to about 99.5% by weight of the herbicidal salt, without including an excess amount of neutralizing base.

Therefore, the present invention is directed to a method of producing a dry, water-soluble herbicidal salt composition, whereby a herbicidal compound that includes a carboxylic acid functionality, such as a substituted benzoic acid herbicide or a phenoxy-substituted carboxylic acid herbicide, or bentazon is neutralized from about 98 to about 100 mole percent by a sufficient amount of a first neutralizing base, such as ammonia, a primary amine or alkanolamine, a secondary amine or alkanolamine, a tertiary amine, or an alkaline salt of an alkali metal, in the presence of a sufficient amount of water to mediate the interaction between the herbicidal compound and the neutralizing base, and to form an aqueous slurry or solution of the herbicidal salt including up to about 96% by weight of the herbicidal salt. The water then is removed under controlled conditions of temperature and pressure to provide dry, free-flowing particles of the herbicidal salt composition. The herbicidal salt composition then, if necessary, is interacted further with a sufficient amount of a second neutralizing base, said second neutralizing base either identical to or different from the first neutralizing base, to convert a sufficient amount of any acid form of the herbicidal compound present in the herbicidal salt composition to the salt form. The acid form of the herbicidal compound arises from stripping the ammonia or the alkylamine from the herbicidal salt, and this further interaction with a second neutralizing base provides a solid herbicidal salt composition that is essentially completely soluble in water.

Surprisingly, it has been found that the acid form of the herbicidal compound does not have to be completely neutralized to provide an essentially completely water-soluble herbicidal composition. A water-soluble composition is provided as long as the herbicidal compound is neutralized about 98% mole percent. Accordingly, because an excess amount of amine neutralizing base is not required, a less corrosive and a low odor herbicidal salt composition results. In accordance with an important feature of the present invention, the herbicidal compound used to prepare the water-soluble herbicidal salt composition should be sufficiently free of impurities, such as chlorophenols, phenoxy acid impurities and other organic impurities, in order to provide a water-soluble herbicidal salt composition as dry, solid particles, preferably in a powdered form.

The above and other aspects and advantages of the present invention will become apparent from the following detailed description of the invention.

DETAILED DESCRIPTION OF THE PREFERRED EMBODIMENTS

The present invention is directed to a method of manufacturing an alkylammonium, a hydroxyalkylammonium, ammonium or an alkali metal salt of a herbicidal compound that includes a carboxylic acid functionality or of bentazon. The salt of the herbicidal compound is manufactured in the form of dry, free-flowing particles of an herbicidal salt composition that contains low residual moisture, such as about 3% or less, like about 0.5%, by weight. The herbicidal salt composition, as manufactured, includes from about 90%, and usually about 95%, up to about 99.5% by weight of the active herbicidal salt. The dry herbicidal salt composition prepared by the method of the present invention is stable, and is essentially completely soluble in cold or hot, hard or soft water. In addition, the herbicidal salt composition prepared by the method of the present invention does not have a "fishy" amine odor, and solutions prepared from the herbicidal salt composition are essentially neutral in pH and also lack the fishy odor.

The volume and weight of the active dry herbicidal salt composition prepared by the present method are significantly reduced in comparison to both the presently-available aqueous solution and granular forms of the herbicidal salt, thereby minimizing the size and cost of the shipping container, the cost of shipping and the need to dispose of herbicide containers. Further, the residual water content of the dry herbicidal salt composition produced by the present method has been reduced sufficiently to permit packaging of the herbicidal salt composition in a water-soluble film packet. A water-soluble film packet including the herbicidal salt composition completely dissolves in cold water, within minutes, after the packet is added to a mixing tank or sprayer by the applicator. Thus, it is unnecessary for the applicator to discard empty herbicide containers, and the potential hazards to the environment relating to ground contamination and to non-biodegradability of pesticide residues remaining in the container and of the container itself are eliminated.

In addition, direct contact between the applicator and the herbicidal salt composition is essentially eliminated when the herbicidal salt composition is packaged in a water-soluble packet. Therefore, the potential for applicator exposure to the pesticide is eliminated. The potential for applicator exposure is present when handling an herbicidal salt in a solution or a granular form. As will be demonstrated more fully hereinafter, the solubility of the dry herbicidal salt composition, and the solubility of the water-soluble packet, is essentially complete in cold water, resulting in a true herbicidal solution that is essentially free from suspended and undissolved matter that can plug the nozzles of the sprayer.

The method of manufacturing an alkylammonium, an alkanolammonium, ammonium, or an alkali metal salt of a herbicidal compound that includes a carboxylic acid functionality, as a dry powder, includes the steps of: (a) preparing a solution of slurry of the salt of the herbicidal compound in the presence of water, wherein a sufficient amount of a first neutralizing base neutralizes the herbicidal compound from about 98 to about 100 mole percent; (b) removing the water from the herbicidal salt under controlled conditions to provide a dry herbicidal salt; and (c) adjusting the alkali content of the dry herbicidal salt with a second neutralizing base, if necessary, to provide an essentially completely water-soluble herbicidal salt composition that provides an aqueous solution exhibiting an essentially neutral pH of about 5 to about 7. Any necessary further processing steps, such as adding optional ingredients, like water-softening agents or surfactants; or grinding or screening, to provide a dry, water-soluble herbicidal salt composition having the desired range of particle sizes, such as a powder having a particle size in the range of from about 25μ (micron) to about 5000μ in diameter, then are performed.

It should be understood that the method of the present invention substantially differs from prior methods of preparing a water-soluble herbicidal salt composition. For example, one standard prior method included forming a highly concentrated slurry of the herbicidal compound, then adding a neutralizing base to form the herbicidal salt. The herbicidal salt formed as a block that then was ground to an appropriate particle size. Such an herbicidal salt includes an excess amount of the neutralizing base, and thereby a solution of the herbicidal salt exhibits a high pH; exhibits a "fishy" amine odor, if an amine is the neutralizing base; and includes a relatively high amount, i.e. greater than 3% by weight, of water. The method of the present invention overcomes each of these disadvantages to provide free flowing particles, of low odor, essentially neutral pH and low water content, that rapidly and essentially completely dissolve in water.

It has been found that the above-described general method provides an herbicidal salt composition having one of three distinctly different physical states, i.e., a crystalline powder, an amorphous paste, or a liquid melt, unless various process and starting material parameters are controlled. Accordingly, the method of manufacturing a dry herbicidal salt composition, as a powder, is related to the specific herbicidal salt composition being manufactured, and to the specific physical state formed by herbicidal salt composition after removing the water from the herbicidal salt. For example, it has been found that under the identical drying conditions, including a vacuum of about 27 to about 29 inches of mercury and a maximum herbicidal salt temperature of 160° F. (71° C.), and in the same horizontally-agitated dryer, the dry dimethylamine salts of 2,4-D, MCPP and 2,4-DP formed as medium-sized crystalline powders; whereas the dry dimethylamine salts of MCPA formed as an amorphous solid having a low melting point, and a mixture of MCPA with 2,4-D and 2,4-DP formed as a liquid melt; and whereas the dry potassium salt of a mixture of MCPA with 2,4-D and 2,4-DP formed as an amorphous paste. Therefore, and as will be discussed more fully hereinafter, it is necessary to control process parameters, like the temperature and vacuum conditions employed to remove the aqueous solvent from the herbicidal salt; and to utilize sufficiently pure herbicidal compounds as a starting material, in order to provide dry particles of a herbicidal salt composition including from about 90% to about 99.5% by weight of the active herbicidal salt and less than about 3%, and down to about 0.5%, by weight moisture, and that is essentially completely soluble in cold or warm, hard or soft water.

It should be understood that the present method is useful in manufacturing an alkylammonium, a hydroxyalkylammonium, ammonium or an alkali metal salt of essentially any herbicidal compound including a carboxylic acid functionality or of bentazon. The preferred herbicidal compounds having a carboxylic acid functionality include: (a) the substituted benzoic acid herbicides, and (b) the phenoxy-substituted carboxylic acid herbicides. However, the dry, water-soluble salts of numerous other herbicidal compounds including a carboxylic acid functionality also can be manufactured by the method of the present invention. The following list of herbicidal compounds is provided to demonstrate examples of compounds that can be converted from a water-soluble acid form to an essentially completely water-soluble salt form. Therefore, examples of suitable herbicidal compounds include, but are not limited to:

(a) substituted benzoic acid herbicides:

2.methoxy-3,6-dichlorobenzoic acid (dicamba),
3,5,6-trichloro-o-anisic acid (tricamba),
3-amino-2,5-dichlorobenzoic acid (amiben),
5-2[2-chloro-4-(trifluoromethyl)phenoxy]-2-nitrobenzoic acid (acid form of acifluorfen),
2,3,5-triiodobenzoic acid, and trichlorobenzoic acid;

(b) phenoxy-substituted carboxylic acid herbicides:

2,4-dichlorophenoxyacetic acid (2,4-D),
2,4-dichlorophenoxybutyric acid (2,4-DB),
2-(2,4-dichlorophenoxy)propionic acid (2,4-DP),
2,4,5-trichlorophenoxyacetic acid (2,4,5-T),
2-(2,4,5-trichlorophenoxy)propionic acid (silvex),
4-chloro-2-methylphenoxyacetic acid (MCPA), 2-(4-chloro-2-methylphenoxy)propionic acid (MCPP),
4-(4-chloro-2-methylphenoxy)butyric acid (MCPD), and
2-[4-(2',4'-dichlorophenoxy)phenoxy]propanoic acid (diclofop); and (c) other herbicidal and related compounds including a carboxylic acid functionality:

2,2-dichloropropionic acid (dalapon),
7-oxabicyclo[2.2.1]heptane 2,3-dicarboxylic acid (endothall),
(2,3,6-trichlorophenyl)acetic acid (fenac),
glufosinate,
gallic acid,
gibberellic acid,
3 indoleacetic acid (growth regulator),
indole-3-butyric acid (growth regulator),
1-naphthaleneacetic acid (growth regulator),
β-naphthoxyacetic acid,
N-(phosphonomethyl)glycine (glyphosate),
4-amino-3,5,6-trichloropicolinic acid (picloram),
3,5,6-trichloro-2-pyridinyloxyacetic acid (triclopyr), and
9-undecylenic acid.

In addition, it has been found that the herbicide bentazon, having the structure depicted in structural formula I also can be converted to an essentially completely water-soluble salt form.

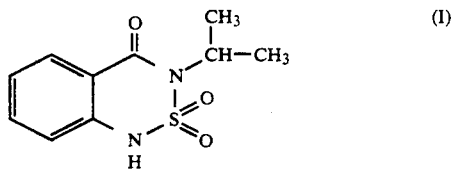

In the case wherein ammonia, an alkylamine or a hydroxyalkylamine is used as the neutralizing base to interact with an herbicidal compound that includes a carboxylic acid functionality, the interaction is a simple acid-base neutralization reaction, wherein the ammonia, the alkylamine or the hydroxyalkylamine, in the presence of water, converts the herbicidal compound including a carboxylic acid functionality into a salt. The reaction is illustrated below in Equation 1, wherein $R_1$, $R_2$, and $R_3$ are, independently, hydrogen, or an alkyl group or hydroxyalkyl group including from one to about four carbon atoms, and wherein $R_4$ is the residue of the herbicidal compound. A similar reaction occurs when the herbicidal compound is interacted with an alkaline salt of an alkali metal, like potassium hydroxide.

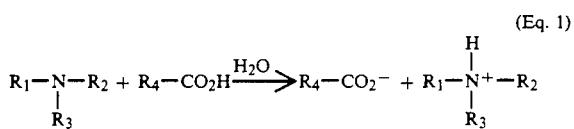

Other suitable amines include morpholine, pyridine, and similar aliphatic and aromatic cyclic amines. In general, any primary, secondary or tertiary amine, either aliphatic or aromatic, can be used as the neutralizing base provided the amine is sufficiently alkaline to neutralize the herbicidal compound, and provided the resulting herbicidal salt is water-soluble. Accordingly, long chain alkylamines and hydroxyalkylamines, i.e., a chain length of greater than about four carbon atoms, generally are unsuitable because the resulting herbicidal salt is insufficiently soluble in water. Examples of useful alkaline salts of an alkali metal include, but are not limited to, sodium hydroxide, potassium hydroxide, potassium carbonate, sodium carbonate, potassium bicarbonate, sodium bicarbonate and combinations thereof.

It should be understood that sufficient water is included in the interaction illustrated in Equation to permit the neutralizing base to interact with the carboxylic acid functionality of the herbicidal compound. It is preferred that a minimum amount of water is used in the neutralization interaction, because less water then needs to be removed from the aqueous reaction mixture to provide a dry herbicidal salt. It also is preferred that water is essentially the only solvent for the herbicidal salt. An excess amount of water is not detrimental to the neutralization interaction, and therefore an upper limit on the amount of water present in the neutralization step is not critical. It is envisioned that in some instances, particularly wherein the acid form of the herbicidal compound is neutralized in its molten state, less than 1% water is needed for the neutralization interaction to proceed sufficiently to provide a dry water-soluble salt composition. Usually, however, at least about 4% water, and usually at least about 10% water, based on the total combined weight of the herbicidal compound, the neutralizing base and the water, is needed for the neutralization reaction to proceed to completion in a relatively short time.

It is know that if the neutralizing base used to interact with the herbicidal compound to form the herbicidal salt is ammonia or a volatile alkylamine, like dimethylamine or ethylamine, then, when the water is removed from the herbicidal salt to form the dry herbicidal salt composition, a portion of the ammonia or the volatile alkylamine also is stripped from the herbicidal salt. As used here, and hereinafter, the term "volatile amine" is defined as a primary, secondary or tertiary amine, either aliphatic or aromatic, and either cyclic or acyclic, that has a boiling point of about 100° C. or less.

Accordingly, by stripping the ammonia or the volatile amine from the herbicidal salt composition, the acid form of the herbicidal compound is partially regenerated. The regeneration of the acid form of the herbicidal compound is disadvantageous because the herbicidal compound generally is water-insoluble in the acid form, and, if the acid form of the herbicidal compound is present in the herbicidal salt composition in a sufficiently large quantity, then the herbicidal salt composition does not demonstrate an essentially complete water solubility.

Therefore, the removal of water from the herbicidal salt is performed under sufficiently mild conditions, such as at a low temperature and, preferably at reduced pressure, in order to minimize the loss of ammonia or volatile alkylamine from the herbicidal salt. Accordingly, it has been found that an aqueous solution of an ammonium or a volatile alkylammonium herbicidal salt should be subjected to sufficiently low drying temperatures such that the herbicidal salt does not attain a temperature in excess of about 80° C. Preferably, therefore, in order to speed the process of removing water from the herbicidal salt, and in order to maintain the drying temperature as low as possible, the water is removed from the herbicidal salt by heating the aqueous solution of the herbicidal salt under a vacuum, and preferably a vacuum of not less than about 20 inches of mercury.

It also has been found that after the water is removed from various particular herbicidal salts, the herbicidal salts do not form into dry, solid particles, but rather form into a molten salt that can be cooled to room temperature without solidifying. It has been determined that this supercooling-type of phenomena can be attributed partially to chemical impurities present in the acid form of the herbicidal compound starting material. Accordingly, in order to provide a solid herbicidal salt composition as discrete, dry particles, it is necessary to utilize an herbicidal compound starting material having a minimum of impurities.

For example, in the manufacture of the herbicidal compound, 2,4-dichlorophenoxyacetic acid (2,4-D), the compound 2,4-dichlorophenol is condensed with monochloroacetic acid to produce 2,4-D. In this process, the impurities in the monochloroacetic acid, such as acetic acid and dichloroacetic acid, and in the 2,4-dichlorophenol, such as unsubstituted phenol and other chlorophenol isomers including monochlorophenol, 2,6-dichlorophenol and 2,4,5-trichlorophenol, either remain in the 2,4-D as unreacted impurities; or they react to form chlorophenoxyacetic acid species other than 2,4-D, and remain in the 2,4-D as reaction impurities. These reaction impurities and some unreacted chlorophenols, including 2,4-dichlorophenol, are the principal impurities in the 2,4-D starting materials.

Some of the impurities in 2,4-D have a lower melting point than 2,4-D. For example, 2,4-dichlorophenol has a melting point of 45° C., whereas pure 2,4-dichlorophenoxyacetic acid (2,4-D) has a melting point of 142° C. Thus, it has been found that the dimehtylamine salt of 2,4-D manufactured according to the present method from 2,4-dichlorophenoxyacetic acid that contains less that about 7% total impurities, and preferably less than about 1.2%, in total, of 2,4-dichlorophenol and other unreacted chlorophenols as impurities solidifies quickly after removing the water and cooling the dimethylamine 2,4-D salt; whereas a 2,4-D acid starting material including more than about 7% total impurities, especially more than about 1.2%, in total, of 2,4-dichlorophenol and other unreacted chlorophenols does not solidify into a particulate solid. Similarly, it has been found that a dimethylamine salt of 2,4-D prepared from a 2,4-D acid starting material including less than about 0.7% of phenoxyacetic acid reaction impurities solidifies quickly after drying and cooling; whereas a dimethylamine salt of 2,4-D acid starting material including more than about 1.0% of phenoxyacetic acid reaction impurities does not solidify into particles of a dry herbicidal salt. A similar supercooling phenomena is observed for phenoxy herbicides other than 2,4-D, in that the ammonium and alkylammonium salts of the phenoxy herbicides tend to supercool rather than form dry particles when the level of impurities in the starting material phenoxy acid exceeds the above stated limits.

In addition, it also has been found that the method of removing the water from the herbicidal salt can influence the solidification of the herbicidal salt composition. For example, in a horizontal cylindrical batch dryer fitted with mixing blades mounted on an axially rotating shaft and having high speed chopping blades mounted radially, the dimethylamine salt of 2,4-D solidified as a hard crystalline powder after a sufficient amount of the water was removed, i.e., after the dimehtylamine salt of 2,4-D included less than about 4% by weight water. The phase change from liquid to solid is rapid when the herbicidal salt composition is dried to include about 3% water. The rapid phase change is demonstrated by a rapid 5° F. drop in temperature as the crystals form, and by a substantially increased torque on the chopping blades.

Conversely, in a continuous thin-film dryer having a high-speed, close-clearance rotor, the dimethylamine salt 2,4-D dried as a viscous melt that slowly solidified over a several day period to provide an herbicidal salt composition having a waxy and soft surface. Furthermore, when a viscous melt of the dimethylamine salt of 2,4-D was cooled and agitated in a scraped, surface heat exchanger, a thick amorphous paste was produced that again exhibited a waxy and soft surface. Thus, the method of agitation, and the resulting energy imparted to the aqueous solution of the herbicidal salt, can influence the physical state of the dried herbicidal salt composition, and can influence the amount of time needed to provide a solid herbicidal salt composition.

Finally, it has been found that the water solubility of the solid ammonium, alkylammonium and hydroxyalkylammonium salts of a herbicidal compound including a carboxylic acid functionality is related to the pH exhibited by a water solution of the herbicidal salt. For example, the dry dimethylamine salt of 2,4-D is essentially completely soluble in cold water when a solution of the dimethylamine 2,4.D salt demonstrates a pH of 5 or above. However, after removing the water from an alkylammonium or an ammonium salt of a phenoxy-substituted carboxylic acid, even under the mild vacuum drying conditions, it has been found that an aqueous solution of the herbicidal salt can demonstrate a pH substantially less than 5 and therefore exhibit incomplete solubility of the herbicidal salt composition as indicated by a milky or hazy appearance of the aqueous solution due to the presence of the water-insoluble acid.

The incomplete water solubility of the herbicidal salt composition is corrected by the addition of a sufficient amount of the neutralizing base to the dry herbicidal salt in the presence of as little as 1% water, to replenish the neutralizing base stripped from the herbicidal salt during the removal of the water. A sufficient amount of neutralizing base has been added when an aqueous solution of the herbicidal salt exhibits a pH in the range of from about 5 to about 7. Accordingly, the water-soluble acid form of the herbicidal compound again is converted to the water-soluble salt form. Such a result is unexpected because, normally, this conversion is performed in an aqueous solution and utilizes an excess amount of neutralizing base to provide a composition that exhibits a pH of about 9 and has an offensive odor.

It also should be understood that optional ingredients can be added to the herbicidal salt composition. For example, after forming dry particles of the herbicidal salt composition, a water-softening, or sequestering, agent can be added to the herbicidal salt composition. It has been found that, although the herbicidal salt composition is essentially completely soluble in hard water having up to about 2000 ppm (parts per million) hardness, including up to about 1% by weight of a suitable water-softening agent ensures that the formation of the water-insoluble calcium and magnesium salts of the herbicidal compound will not occur. Accordingly, suitable water-softening compounds include, but are not limited to, sodium lignosulfonates; aminocarboxylic acids, like ethylenediaminetetraacetic acid and nitrilotriacetic acid; polycarboxylic acids, like citric acid or tartaric acid; phosphonates; and similar water-softening agents well-known to those skilled in the art.

Another optional ingredient, included in the herbicidal salt composition in an amount ranging up to about 2% by weight of the composition, is a surfactant to help disperse the herbicidal salt in water and to help the herbicidal salt more effectively penetrate the leaf of sprayed vegetation. The surfactant is an anionic, an amphoteric or a nonionic surfactant, wherein the identity of the surfactant is not limited provided that the surfactant does not adversely affect either the water-solubility of the herbicidal salt composition or the ability of the herbicidal salt composition to eradicate susceptible vegetation. Cationic surfactants should be avoided because of the anionic nature of the herbicidal salt composition. Likewise, other optional ingredients, like anticaking agents, that do not adversely affect either the water solubility or the herbicidal effectiveness of the herbicidal salt composition also can be included in the herbicidal salt composition.

Therefore, in accordance with an important feature of the present invention, a water-soluble herbicidal salt composition, in solid form, and preferably in powdered form, and including from about 90% to about 99.5%, and generally from about 95% to about 99.5%, of the herbicidal salt composition, and less than about 3% water, and generally less than about 1% water, can be manufactured by controlling process parameters, such as the temperature and pressure utilized to remove excess water; by utilizing a sufficiently pure herbicidal compound including a carboxylic acid functionality or bentazon as a starting material; and, if necessary, by the addition of a sufficient amount of a neutralizing base to the dry herbicidal salt composition to replace the ammonia or volatile alkylamine stripped from the herbicidal salt composition during the drying process.

In general, and as will be demonstrated more fully in the following examples, a method of manufacturing an essentially completely water-soluble herbicidal salt composition including less than about 3%, like about 0.5%, by weight water, and at least about 90%, usually at least about 95%, and up to about 99.5% by weight of the herbicidal salt, in a dry solid form, first requires a herbicidal compound including a carboxylic acid functionality having a minimum amount of impurities as a starting material. As previously stated, the acid form of the herbicidal compound should contain less than about 7% by weight total impurities, and preferably less than about 1.2% of unreacted impurities, like chlorophenols, and less than about 0.7% of reaction impurities. For example, in the case of 2,4-D acid, the starting material, in the acid form, should include less than about 1.2% of 2,4-dichlorophenol and other unreacted phenols; and less than about 0.7% of bis 2,4.D acid, sodium 2,4-D and other phenoxyacetic acid reaction impurities. Herbicidal compounds, in the acid form, including greater amounts of unreacted and reaction impurities often cannot solidify after interaction with a neutralizing base, and removal of water, to provide dry, solid particles of the herbicidal salt composition.

The acid form of the herbicidal compound then is interacted with a neutralizing base, like ammonia, an alkylamine, a hydroxyalkylamine or an alkaline salt of an alkali metal, in the presence of water, to form a solution, a slurry, or a melt of the herbicidal salt composition. In this neutralization interaction, a minimum amount of water, for example as low as about 4% water by weight, is used. The amount of water however is sufficient such that the acid form of the herbicidal compound is neutralized from about 98 to about 100 mole percent, and is sufficiently low such that the amount of water to be removed from the herbicidal salt composition is minimized. In some cases, the amount of water necessary to effect neutralization is sufficiently great such that a true aqueous solution of the herbicidal salt results; in other cases, a lesser amount of water is needed, and an aqueous slurry of the herbicidal salt results. Also, in other cases, wherein a very small amount of water is necessary to effect neutralization, such as about 4% based on the weight of the herbicidal salt composition, an aqueous melt results. As used here and hereinafter, the term "melt" is defined as a herbicidal salt composition that includes a low amount of water, such as about 4% by weight, but does not solidify into dry, solid particles without further processing.

The amount of water needed in the neutralization of the acid form of the herbicidal compound is related to the identity of the herbicidal compound and is related to the identity of the neutralizing base, i.e. ammonia, an alkylamine, a hydroxyalkylamine or an alkaline salt of an alkali metal. As previously stated, a suitable alkylamine or hydroxyalkylamine includes, for example, a primary, a secondary or a tertiary amine having alkyl groups including from one to about four carbon atoms. The preferred alkylamine and hydroxyalkylamine neutralizing bases for the acid form of the herbicidal compound include ammonia, dimethylamine, isopropylamine, trimethylamine, ethanolamine, diethanolamine and combinations thereof. To achieve the full advantage of the present invention, the neutralizing base is dimethylamine or diethanolamine. Potassium hydroxide, sodium hydroxide, potassium carbonate, potassium bicarbonate, sodium carbonate, sodium bicarbonate, and combinations thereof also are suitable neutralizing bases. It should be understood that excess water can be included in the interaction between the neutralizing base and the acid form of the herbicidal compound. However, more water then must be removed to provide a solid herbicidal salt composition.

The aqueous solution, slurry or melt of the herbicidal salt then is charged into a suitable dryer to remove the water. Preferably, the dryer can be heated, and can be subjected to a vacuum to facilitate the removal of the water from the herbicidal salt composition. However, in the case of an ammonium salt, or of a salt including a volatile alkylamine, the water removal process step should be controlled such that the temperature of the herbicidal salt does not exceed about 80° C., otherwise excess amounts of ammonia or the volatile alkylamine are stripped from the herbicidal salt. If excess amounts of ammonia or the volatile alkylamine are stripped from the herbicidal salt, then the stripped ammonia or volatile alkylamine amine can be replenished after the water is removed from the herbicidal salt composition.

During the water-removal step, the herbicidal salt composition forms into one of three physical states, depending upon the particular herbicidal salt composition being dried. In some instances, such as for the alkylamine salts of 2,4-D, MCPP and 2,4-DP, the herbicidal salt composition, after removing the water and cooling, forms into a medium-sized crystalline solid. Then, the herbicidal salt composition is simply discharged from the dryer and subjected to conventional processing steps, such as the addition of optional ingredients, grinding, milling, screening and packaging. In this particular case, after the herbicidal salt composition has formed into a solid in the dryer, a sufficient amount of the neutralizing base, in a minimum amount of water, can be added to the solid herbicidal salt composition to replenish any volatile alkylamine stripped from the herbicidal salt composition during the water-removal step. Accordingly, essentially complete water solubility of the herbicidal salt composition is assured.

In another instance, such as in the manufacture of the potassium salt of the various phenoxy herbicides, if the herbicidal salt composition is dried completely in the dryer, then the herbicidal salt composition forms into a very hard solid mass. Accordingly, the water removal step is interrupted when the herbicidal salt composition forms a slurry that generally still includes from about 4% to about 10% by weight water. The slurry of the herbicidal salt composition then is removed from the drier and is allowed to dry slowly under normal atmospheric conditions, or under conditions of slightly elevated temperature, such as on a tray, to provide a dry, solid herbicidal salt composition. The herbicidal salt composition then is subjected to conventional processing steps such as the addition of optional ingredients, grinding, screening and packaging.

In the third instance, such as in the manufacture of the dimethylamine salt of MCPA, the herbicidal salt composition, after removal of the water and replenishment of the stripped dimethylamine, exits the dryer as a viscous liquid melt including from about 1% to about 4% water. It has been found that continued drying of such a viscous liquid melt does not provide a dry, solid herbicidal salt composition. Therefore, the viscous liquid herbicidal salt composition is removed from the dryer and placed on trays to dry slowly, under atmospheric conditions, over a period of several days to provide a dry, solid herbicidal salt composition. It also has been found that an attempt to accelerate this final drying process step does not yield a dry, solid herbicidal salt composition. However, after slow drying over a period of several days, the resulting herbicidal salt composition is dry to the touch, and can be processed normally by grinding, screening and packaging.

In each of the three above-discussed instances, the resulting herbicidal salt composition is sufficiently dry to be packaged in a water-soluble packet, such as a packet comprising a polyvinyl alcohol film. The water-soluble packet is not adversely affected by the herbicidal salt composition because the salt is dry to the feel and includes less than about 3%, and usually less than 1%, by weight water. Furthermore, when the herbicidal salt is to be applied to a crop or turf, the water-soluble packet simply is added to a sufficient amount of water, and the water-soluble packet and herbicidal salt composition dissolve essentially completely, without agitation, to provide a ready-to-use solution of the herbicidal salt.

To demonstrate the new and unexpected results demonstrated by the method of the present invention, the following Examples have been provided as illustrations of dry, solid herbicidal salt compositions prepared by the above-described method.

EXAMPLE 1

Summary of Drying Tests Performed on Aqueous Solutions of Various Salts of Phenoxy Herbicides In general, an aqueous solution of a water-soluble salt of a phenoxy herbicide, like 2,4-D, was charged into a batch vacuum dryer including a horizontal cylindrical vessel equipped with an external steam-heated jacket, and having a central axial rotating shaft fitted with plow-type mixing blades and a radially-mounted high-speed chopping blade mixer. A vacuum of from about 27 to about 29 inches mercury was applied to the dryer by a vacuum pump through a water-cooled vapor condenser and condensate receiver. Steam, at a temperature of about from 110° C. to about 120° C., was applied to the heating jacket. The salt of the phenoxy herbicide in the dryer therefore was subjected to a maximum temperature of about 75° C., and the water present in the aqueous solution was evaporated, condensed, and collected in the condensate receiver. The specific drying conditions for runs 1(a) through 1(d) are summarized below in Table I. As explained more fully below, each of the four runs provided a different result that was related to the conditions used to remove the water and the particular herbicidal salts present in the aqueous solution. In each run, the acid form of the phenoxy herbicide included less than 1.2% of unreacted impurities and less than 0.7% of reaction impurities.

TABLE I

| Run | Herbicidal Salts | % Herbicidal salts (by wt.) | Water (by wt.) | Temperature (°C.) Initial[1] | Final[2] | Jacket | Vacuum (in. Hg) |
|---|---|---|---|---|---|---|---|
| 1(a) | Potassium salts of MCPP; MCPA; and dicamba[3] | 80 | 20 | 46 | 76 | 110/121 | 26 |
| 1(b) | Potassium salts of MCPA, 2,4-DP and MCPP[4] | 75 | 25 | 49 | 68 | 110 | 26.5 |
| 1(c) | Dimethylamine salt of 2,4-D[5] | 83 | 17 | 49 | 74.5 | 110 | 25/27 |
| 1(d) | Dimethylamine salt of 2,4-D[5] | 83 | 17 | 49 | 77 | 110 | 24.5/ 26.5 |

[1]initial temperature of herbicidal salt solution charged into the dryer;
[2]final temperature attained by the herbicidal salt solution during the run;
[3]a solution including 21.3% potassium salt of MCPP; 53.4% potassium salt of MCPA; and 5.3% potassium salt of dicamba;
[4]TRIAMINE ® II WS, available commercially from Riverdale Chemical Co., Glenwood, IL, including 17% potassium salt of MCPA, expressed as acid equivalent; 17% potassium salt of 2,4-DP, expressed as acid equivalent, and 17% potassium salt of MCPP, expressed as acid equivalent; and
[5]a solution including about 83% dimethylamine salt of 2,4-D.

Run 1(a)—a charge of 100 pounds (lbs.) of the aqueous herbicidal salt solution including 20% water was dried in the dryer. The run was terminated because a high power load developed on the plow and chopper drives. The heated surfaces of the dryer were heavily-coated with a hard layer of herbicidal salt composition, whereas the unheated surfaces were free of the herbicidal salt composition. The herbicidal salt composition was a very viscous, rubbery "dough-like" material, of a fine crystalline nature, that did not form into a readily friable solid after cooling.

Run 1(b)—a 30 lb. heel of previously prepared lumps of the herbicidal salt composition was added to the dryer. The lumps were quickly pulverized by the chopping blade before the feed solution, including 25% water, was drawn under vacuum in the dryer in increments. After 19 lbs. of the aqueous solution was added to the dryer over a 35 minute period, the run was terminated because a high power load developed on the plow drive. Similar to run 1(a), the herbicidal salt composition was a viscous, rubbery "dough-like" material, and the heated surfaces were coated with a layer of the herbicidal salt composition.

Run 1(c)—a charge of 150 lbs. of the aqueous herbicidal salt solution, including 17% water, was added to the dryer, and was dried in 50 minutes. The change to a crystalline state was clearly indicated by an endothermic cooling of about 5.5° C. The herbicidal salt composition was a "brown sugar-like", medium-sized crystalline solid. The heated surfaces of the dryer were clean, and the unheated surfaces were coated with the herbicidal salt composition. The herbicidal salt composition dissolved in cold water to form a clear solution, without the need for any adjustment with dimethylamine. Water cooling was slow (76° C. to 59.5° C. in 20 minutes), and was even further slowed as the energy input of the plow mixer balanced the water cooling rate. Upon standing overnight, the herbicidal salt composition agglomerated in a plastic lined fiber keg, and was easily comminuted.

Run 1(d)—a charge of 122 lbs. of the aqueous herbicidal salt solution was added to the dryer, and was dried in 40 minutes. The heated surfaces of the dryer were free of the herbicidal salt composition. The batch was water-cooled for 7 minutes (77° C. to 70.5° C.) before liquid nitrogen was injected into the dryer (15 lbs. of nitrogen in 1 to 2 minutes). The liquid nitrogen cooled the batch from 70.5° C. to 31° C. The herbicidal salt composition changed from a "brown sugarlike" material to a mixture of fine powder and large agglomerated lumps. This mixture probably resulted due to cooling the herbicidal salt composition too rapidly with nitrogen.

Runs 1(c) and 1(d) illustrate that an aqueous solution including the dimethylamine salt of the phenoxy-herbicides can be dried to a "brown sugar-like" crystalline powder, but should be cooled to below 38° C. to minimize the tendency to agglomerate. The addition of an inert anticaking agent, such as fumed silica, calcium silicate or a noncrosslinked polyacrylic acid resin, into the dryer could further reduce the tendency of the herbicidal salt composition to agglomerate. Cooling the herbicidal salt composition in the dryer to temperatures below 60° C. is slow due to the energy input from the plow drive. The injection of liquid nitrogen, at a slower, more controlled rate than that used in run 1(d), or external cooling with liquid nitrogen or refrigerated air, is an effective and economical way to cool dried batches. Alternatively, a truck or tray, shelf or fluidized bed cooler can be used to cool the herbicidal salt composition.

Runs 1(a) and 1(b) show that proper process steps are required to dry an aqueous herbicidal salt solution to a solid, particulate herbicidal salt composition. In these runs, after removing the water, a thick and viscous paste is formed that coats the heated surfaces and causes overloading of the plow and chopper drives. It has been theorized that the high mixing energy input causes the formation of a fine crystalline structure as a paste that is soft and sticky at a temperature in the range of about 65.5° C. to about 76.5° C. However, the dryer can be used to manufacture herbicidal salt compositions using technical phenoxy acids and caustic potash flake, with little additional water. These potassium-based herbicidal salt compositions can be dried slowly in a tray or shelf dryer to provide a hard solid.

In addition to the above runs 1(a) through 1(d), an aqueous solution of the dimethylamine salts of 2,4-D, 2,4-DP and MCPP was dried in the above-described mixer. The solution formed a viscous liquid melt that formed into a hard solid when allowed to cool slowly without a high mixing energy input.

The herbicidal salt composition including a combination of the dimethylamine salts of 2,4-D, 2,4-DP and MCPP slowly formed into a dry product. In order to provide a dry product more quickly, the dry, solid dimethylamine salts of 2,4-D, 2,4-DP and MCPP each are prepared individually, then dry blended to provide a dry herbicidal salt composition including the desired amounts of the dimethylamine salts of 2,4-D, 2,4-DP and MCPP. Other herbicidal salt compositions that include more than one herbicidal compound similarly can be produced more rapidly by preparing the individual herbicidal salts, then combining the herbicidal salts to provide the desired herbicidal salt composition.

EXAMPLE 2

Preparation of the Dimethylamine Salt of 2,4-D (Batch Process)

The dimethylamine salt of 2,4-D was prepared by reacting dimethylamine, in the presence of water, with a 2,4-D acid having the following specifications:

| | | |
|---|---|---|
| 2,4-D acid active isomer (by weight) | 97% (as is basis) | |
| Other phenoxy acids | 0.2% | |
| bis - 2,4-D acid | 0.4% | (0.69% total) |
| Sodium 2,4-D | 0.09% | |
| 2,4-dichlorophenol and other phenol impurities | 1.2% | |
| Sodium chloride | 0.02% | |
| Free acid (as HCl) | 0.40% | (0.425%) |
| Sodium sulfate | 0.005% | |
| Water | <1.0% | |
| Sodium salts (total) | 0.115%. | |

The resulting aqueous solution included 83% by weight of the dimethylamine salt of 2,4-D and had a pH of about 8.3. The aqueous solution of the dimethylamine salt of 2,4-D (150 parts by weight), at a temperature of about 50° C., was charged into a batch vacuum dryer including a horizontal cylindrical vessel equipped with an external steam heated jacket, and having a central axial rotating shaft fitted with plow-type mixing blades and a radially-mounted high-speed chopping blade mixer. A vacuum of from about 27 to about 29 inches mercury was applied to the dryer by a vacuum pump through a water-cooled vapor condenser and condensate receiver. Steam, at a temperature of about 110° C., was applied to the heating jacket. The dimethylamine salt of 2,4-D in the dryer was subjected to a maximum temperature of about 75° C., and the water present in the aqueous solution was evaporated, condensed, and collected in the condensate receiver. After about 50 minutes, a total of 18.3 parts by weight of water were collected in the condensate receiver. Heating of the dimethylamine salt of 2,4.D then was stopped, and cooling water, at about 15° C., was run through the heating jacket of the dryer. After about 20 minutes, the dimethylamine 2,4-D salt in the dryer had cooled to about 58° C. The dry, solid dimethylamine salt of 2,4-D in the dryer included about 1 2% by weight water, and the herbicidal salt composition was a free-flowing, crystalline powder that dissolved completely and quickly in cold water, without agitation, to form a clear aqueous solution having a pH value of 5.5. The herbicidal salt composition was assayed and found to include 96.9% of the dimethylamine salt of 2,4-D.

EXAMPLE 3

Preparation of the Dimethylamine Salt of 2,4-D (Batch Process)

The method described in Example 2 was repeated, except the steam heating jacket was heated to a temperature of about 120° C., and, accordingly the dimethylamine 2,4-D salt was subjected to a maximum temperature of about 90° C. The dried dimethylamine 2,4-D salt was a free-flowing, crystalline powder including about 0.3% water by weight, and formed a milky solution in cold water. The milky aqueous solution demonstrated a pH value of about 4.5 because the higher process temperature stripped a portion of the dimethylamine from the herbicidal salt, and therefore, the acid-form of 2,4-D was present in the herbicidal salt composition. Then, three parts by weight of a 60% aqueous solution of dimethylamine were charged into the dryer and mixed with the dried dimethylamine 2,4-D salt composition for about 2 minutes. A sample of the resulting dimethylamine 2,4-D salt composition then was tested for solubility in cold water, and was found to be essentially completely water-soluble providing a clear solution having a pH value of 5.5.

EXAMPLE 4

Preparation of the Dimethylamine Salt of 2,4-D (Continuous Process)

An aqueous solution of the dimethylamine salt of 2,4-D, having a water content of 21%, was prepared as described in Example 2. The aqueous solution of the dimethylamine 2,4-D salt was heated to about 50° C., then fed continuously into an agitated thin-film evaporator at a rate of about 225 parts per hour. The thin-film evaporator was under a vacuum of about 27.5 inches of mercury, and had a steam-heated jacket temperature of about 128° C. The dimethylamine 2,4-D salt was subjected to a maximum temperature of about 93° C. The dimethylamine salt of 2,4-D, including about 1.5% by weight residual water, was discharged from the evaporator as a pumpable slurry including fine crystals. An aqueous solution of the dimethylamine 2,4-D salt demonstrated a pH value of 4.3, and the aqueous solution was milky due to the presence of water-insoluble 2,4-D acid. Therefore, two parts of a 60% aqueous solution of dimethylamine were added to the slurry before the slurry was allowed to cool over a 15 minute period. After cooling, a lumpy, hard crystalline solid formed. The solid dimethylamine 2,4-D salt was comminuted to provide a free-flowing powder of the herbicidal salt composition that was essentially completely soluble in cold water to provide a clear solution having a pH value of about 5.

EXAMPLE 5

Preparation of the Dimethylamine Salt of a Mixture of 2,4-D, MCPA and MCPP (Batch Process)

An aqueous solution (144 parts) including equal amounts of the dimethylamine salts of MCPA, MCPP, and 2,4-D, and including 17.5% by weight water, was charged into a batch vacuum dryer at 50° C. as described in Example 2. A vacuum of about 27 inches of mercury was applied to the dryer, and the steam jacket was heated to a temperature of about 90° C. Water present in the aqueous solution was evaporated, condensed, and collected over a period of about 3 hours. The resulting dimethylamine 2,4-D salt composition formed into a melt that contained 4% by weight water. The melt was allowed to cool slowly, with slight agitation, over a period of about 24 hours. During this period, the melt formed into a hard, crystalline solid of the herbicidal salt composition that was comminuted into a free-flowing powder. The powder of the herbicidal salt composition essentially completely dissolved in cold water to form a clear solution having a pH value of 5.

EXAMPLE 6

Preparation of the Dimethylamine Salt of a Mixture of 2,4-D, MCPA and MCPP (Continuous Process)

An aqueous solution, as identified in Example 5 and including 17.5% by weight water, was fed continuously, at a rate of 218 parts per hour, into an agitated thin.film evaporator. The evaporator was under a vacuum of 28 inches of mercury and was equipped with a steam-heated jacket heated to a temperature of about 110° C. Water was removed from the herbicidal salt solution to provide an herbicidal salt composition having a residual water content of about 3.1% by weight. The herbicidal salt composition was discharged from the evaporator as a pumpable liquid melt. The melt was allowed to cool slowly, with slight agitation, and over a 36 hour period. During this time period, the melt formed into a hard, crystalline solid of the herbicidal salt composition. The herbicidal salt composition then was comminuted, followed by grinding into a free-flowing powder. The powder was essentially completely soluble in cold water to form a clear solution having a pH value of 5.

EXAMPLE 7

Preparation of the Potassium Salt of a Mixture of 2,4-D, 2,4-DP and MCPP (Batch Process)

(A) A mixture of the potassium salts of 2,4-D, 2,4-DP, and MCPP (87 parts), in the ratio of 1:1:1, and containing 14% by weight water, at a temperature of about 50° C., was charged into a batch vacuum dryer as described in Example 2. A vacuum of about 27 inches of mercury was applied to the dryer, and the steam-heated jacket was heated to a temperature of about 160° C. After about 1 hour, with the dried herbicidal salt composition having a temperature of about 114° C. and including 7.8% water, the herbicidal salt composition formed into an amorphous paste. After slowly cooling over several days, the herbicidal composition remained as a semi-solid paste. Accordingly, this process was unsuitable for the preparation of a dry free-flowing, potassium salt of an herbicidal compound.

(B) A mixture of the potassium salts of 2,4-D, 2,4-DP, and MCPP was prepared in a heavy duty mixer, equipped with a steam-heated jacket, by charging (a) the dry chlorophenoxy carboxylic acids in the ratio of 1:1:1, (b) the stoichiometric equivalent of caustic potash flake, and (c) 5% water into the mixer, then heating the resulting mixture to about 110° C. After about 15 minutes, the mixture of potassium salts formed into a pumpable slurry that was transferred onto trays. The trays were placed in a heated drying chamber at a controlled temperature of 110° C. After a period of about 24 hours, the mixture of the potassium salts dried and had crystallized into a hard solid of an herbicidal salt composition that was comminuted, then ground to a free-flowing powder. The powder of the herbicidal salt composition was essentially completely soluble in cold water to form an aqueous solution having a pH value of about 7.

In an alternate method, the herbicidal salt compositions of Examples 5 through 7, and in any of the following examples, also can be prepared by forming the individual dimethylamine or potassium salt of each herbicidal compound, then combining the individual herbicidal salts to provide the desired herbicidal salt composition, i.e., individually prepare the dimethylamine salts of 2,4-D, MCPA and MCPP, each by the method set forth in Example 5, then dry blend the three dimethylamine salts to provide the composition of Example 5.

To further demonstrate the new and unexpected results achieved by the method of the present invention, Examples 8 through 14 illustrate dry, water-soluble herbicidal salt compositions prepared by the method.

EXAMPLE 8

Preparation of the Sodium Salt of Bentazon

The sodium salt of bentazon (610 lbs.), including about 47% water, at a temperature of about 50° C., was charged into a batch vacuum dryer including a horizontal cylindrical vessel equipped with an external steam heated jacket, and having a central axial rotating shaft fitted with plow-type mixing blades and a radially-mounted high-speed chopping blade mixer. A vacuum of from about 27 to about 29 inches mercury was applied to the dryer by a vacuum pump through a water-cooled vapor condenser and condensate receiver. Steam, at a maximum temperature of about 110° C., was applied to the heating jacket. The sodium salt of bentazon in the dryer was subjected to a temperature of about 55° C., and the water present in the aqueous solution was evaporated, condensed, and collected in the condensate receiver. After about 2 hours, a total of 275 lbs. of water was collected in the condensate receiver. Heating of the sodium salt of bentazon then was stopped. After about 10 minutes, the sodium bentazon salt in the dryer had cooled to about 30° C. The dry, solid sodium salt of bentazon including about 1.4% by weight water, and the herbicidal salt composition was a yellow, free-flowing, crystalline powder that dissolved completely and quickly in cold water, without agitation, to form a clear aqueous solution having a pH value of 8.2. The herbicidal salt composition was assayed and found to include greater than 90% of the sodium salt of bentazon.

EXAMPLE 9

Preparation of the Potassium Salt of Bentazon

The method described in Example 8 was repeated using the potassium salt of bentazon. The resulting dry, solid product included about 96.2% by weight of the potassium salt of bentazon and dissolved quickly and completely in cold water to form a clear aqueous solution.

EXAMPLE 10

Preparation of the Dimethylamine Salt of 2,4-D

The method described in Example 2 was repeated. Accordingly, a solution of dimethylamine 2,4-D salt (1700 lbs.) was subjected to a maximum temperature of about 75° C. The dried dimethylamine 2,4-D salt (1200 lbs.) was a free-flowing, crystalline powder including about 1.2% water by weight, and formed a hazy solution in cold water. The hazy aqueous solution demonstrated a pH value of about 4.8.

EXAMPLE 11

Preparation of Dimethylamine Salt of 2,4-D

The method described in Example 2 was repeated using a solution of the dimethylamine of 2,4-D (2020 lbs.) including 69% by weight of the herbicidal salt. The dried dimethylamine 2,4-D salt was free-flowing, crystalline powder including about 0.6% water by weight, and formed a hazy solution in cold water. The hazy solution demonstrated a pH value of about 4.7.

EXAMPLE 12

Preparation of the Dimethylamine Salt of 2,4-D

The method described in Example 10 was repeated, and provided a free-flowing, crystalline powder including a free-flowing, crystalline powder including about 0.8% water by weight, and formed a clear solution in cold water. The clear solution demonstrated a pH value of about 5.2.

EXAMPLE 13

Preparation of the Diethanolamine Salt of MCPP

The method described in Example 2 is repeated using an aqueous solution (2200 lbs.) including about 46% by weight of the diethanolamine salt of MCPP. After removing the water, a free-flowing crystalline powder of the diethanolamine salt of MCPP (1023 lbs.), including about 1.0% water, is removed from the dryer. An aqueous solution is prepared from the solid diethanolamine salt of MCPP, and demonstrates a pH of 4.2 and is cloudy. The solution is clarified by adding a sufficient amount of diethanolamine to the diethanolamine salt of MCPP to provide a solution having a pH of 4.8.

EXAMPLE 14

Preparation of the Dimethylamine Salts of a Mixture of 2,4-D, 2,4-DP and MCPP An aqueous solution (2311 lbs.) including the dimethylamine salts of 2,4-DP (404 lbs.), MCPP (423 lbs.) and 2,4-D (850 lbs.) and including 47.5% by weight water, was charged into a batch vacuum dryer at 50° C. as described in Example 2. A vacuum of 27 inches of mercury was applied to the dryer, and the steam jacket was heated to a maximum temperature of about 120° C. Water present in the aqueous solution (1180 lbs.) was evaporated, condensed, and collected over a period of about 2.5 hours. The resulting dimethylamine salt composition (1250 lbs.) was a free-flowing, crystalline solid of the herbicidal salt composition, including 47% by weight dimethylamine salt of 2,4-D, 23.8% by weight dimethylamine salt of 2,4-DP, 24.2% by weight dimethylamine salt of MCPP, and 3.1% by weight water. The powder of the herbicidal salt composition essentially completely dissolved in cold water to form a hazy solution having a pH value of 4.1.

EXAMPLE 15

Preparation of the Diethanolamine Salt of 2,4-D

The method described in Example 2 is repeated using an aqueous solution of the diethanolamine salt of 2,4-D. The dried diethanolamine salt of 2,4-D is a free-flowing crystalline powder including about 0.5% by weight water, and forms a cloudy solution in water. The cloudy solution has a pH of about 4.3, and is clarified by adding a sufficient amount of diethanolamine to the aqueous solution of the diethanolamine salt of 2,4-D to provide a solution having a pH of about 5.

EXAMPLE 16

Preparation of the Potassium Salts of a Mixture of 2,4-D, MCPP and Dicamba

The method of described in Example 7(B) was repeated using an aqueous solution including a mixture of the potassium salts of 2,4-D, MCPP and dicamba, present in a stoichiometric ratio of 11:6:1. The resulting potassium salt composition was a free-flowing, crystalline solid including greater than 90% by weight of the potassium salts of 2,4-D, MCPP and dicamba. The solid herbicidal salt composition dissolved essentially completely in cold water.

EXAMPLE 17

Preparation of the Dimethylamine Salts of a Mixture of 2,4-D, MCPP and Dicamba The method described in Example 2 was repeated on an aqueous solution including 30.6% dimethylamine salt of 2,4-D, 16.3% dimethylamine salt of MCPP and 2.8% dimethylamine salt of dicamba, by weight. The resulting dimethylamine salt composition was a free-flowing, crystalline solid including greater than 90% by weight of the dimethylamine salts of 2,4-D, MCPP and dicamba. The solid product dissolved essentially completely in water to provide a clear solution.

EXAMPLE 18

Preparation of the Ammonium Salt of Glufosinate

The method described in Example 2 was repeated on an aqueous solution including 47% by weight of the ammonium salt of glufosinate. The resulting ammonium salt composition was a free-flowing, crystalline solid including greater than 90% by weight of the ammonium salt of glufosinate. The solid herbicidal salt composition dissolved essentially completely in water to provide a clear aqueous solution.

In each of the above Examples, the resulting herbicidal salt composition was sufficiently dry such that the herbicidal salt composition could be packaged in a water-soluble packet, such as a packet manufactured from a polyvinylalcohol film, without adversely affecting the structural integrity of the film. For example, the herbicidal salt composition prepared in Example 1 was packaged in a polyvinylalcohol packet, and the water-soluble packet maintained its structural integrity for at least a period of 12 months. Such a result is both new and unexpected in the art of herbicidal salt compositions, especially herbicidal salt compositions including ammonia, an alkylamine or a hydroxyalkylamine, because prior art methods of preparing the herbicidal salt composition included a sufficiently high amount of water to attack the water-soluble packet. Such a finding is important in the art because herbicidal salt compositions now are available as a highly-concentrated, water-soluble solid, as opposed to a liquid, such that environmentally-unsafe herbicide containers are eliminated and such that herbicide applicator contact with the concentrated herbicidal compound during preparation of the spraying solution is essentially eliminated.

What is claimed is:

1. A method of preparing a particulate, free-flowing, water-soluble herbicidal salt composition, said herbicidal salt composition including at least about 95% by weight of an herbicidal salt, comprising the steps of:
   (a) forming an aqueous mixture of the herbicidal salt from (i) an herbicidal compound, said herbicidal compound including less than about 7% by weight total impurities, (ii) a sufficient amount of a first neutralizing base to neutralize the herbicidal compound from about 98 to about 100 mole percent, said first neutralizing base selected from the group consisting of ammonia, an alkylamine, a hydroxyalkylamine, an alkaline salt of an alkali metal, and combinations thereof, wherein the alkylamine and the hydroxyalkylamine are primary, secondary or tertiary amines having alkyl groups including one to about four carbon atoms, and (iii) a solvent for the herbicidal salt comprising water as a major component, said aqueous mixture including at least about 4% by weight water;
   (b) evaporating the solvent from the aqueous solution of step (a), while maintaining the temperature of the herbicidal salt below about 80° C., to form the particulate herbicidal salt composition including less than about 3% by weight water; and
   (c) adding a sufficient amount of a second neutralizing base to the herbicidal salt composition formed in step (b) to provide an essentially completely water soluble particulate herbicidal salt composition, wherein an aqueous solution of the herbicidal salt composition has a pH of about 5 to about 7, and wherein the second neutralizing base is selected from the group consisting of ammonia, an alkylamine, a hydroxyalkylamine, an alkaline salt of an alkali metal, and combinations thereof, wherein the alkylamine and the hydroxyalkylamine are primary, secondary or tertiary amines having alkyl groups including one to about four carbon atoms.

2. The method of claim 1, wherein the solvent is evaporated in step (b) at a pressure of less than one atmosphere.

3. The method of claim 1, wherein the herbicidal salt composition includes up to about 99.5% by weight of the herbicidal salt.

4. The method of claim 1, wherein the herbicidal salt composition includes about 0.5% by weight water.

5. The method of claim 1, wherein the herbicidal compound includes a carboxylic acid functionality.

6. The method of claim 5, wherein the herbicidal compound is a substituted benzoic acid herbicide.

7. The method of claim 6, wherein the substituted benzoic acid herbicide is selected form the group consisting of 2-methoxy-3,6-dichlorobenzoic acid, 3,5,6-trichloro-o-anisic acid, 3-amino-2,5-dichlorobenzoic acid, 5-[2-chloro4-(trifluoromethyl) phenoxy]-2-nitrobenzoic acid, 2,3,5-triiodobenzoic acid, trichlorobenzoic acid, and combinations thereof.

8. The method of claim 5, wherein the herbicidal compound is a phenoxy-substituted carboxylic acid herbicide.

9. The method of claim 8, wherein the phenoxy-substituted carboxylic acid herbicide includes less than about 1.2% by weight unreacted chlorophenol impurities and less than about 0.7% reaction impurities.

10. The method of claim 8, wherein the phenoxy-substituted carboxylic acid herbicide is form the group consisted of 2,4-dichlorophenoxyacetic acid, 2,4-dichlorophenoxybutyric acid, 2-(2,4-dichlorophenoxy)-propionic acid, 2,4,5-trichlorophenoxy) propionic acid, 2-(2,4,5-trichlorophnoxy)propionic acid, 4-chloro-2-methylphenoxyacetic acid, 2-(4-chloro-2-methylphenoxy)propionic acid, 4-(4-chloro-2-methylphenoxy)butyric acid, 2-[4-(2', 4'-dichlorophenoxy) phenoxy]-propanoic acid, and combinations thereof.

11. The method of claim 1, wherein the herbicidal compound is bentazon.

12. The method of claim 1, wherein the herbicidal compound is selected from the group consisting of bentazon, 2-methoxy-3,6-dichlorobenzoic acid, 3,5,6-trichloro-o-anisic acid, 3-amino-2,5-dichlorobenzoic acid, 5-[2-chloro-4-(trifluoromethyl)phenoxyl]-2nitrobenzoic acid, 2,3,5-triiodobenzoic acid, trichlorobenzoic acid, 2,4-dichlorophenoxyacetic acid, 2,4-dichlorophenoxybutyric acid, 2-(2,4-dichlorophenoxy)propionic acid, 2,4,5-trichlorophenoxyacetic acid, 2-(2,4,5-trichlorophenoxy)propionic acid, 4-chloro-2-methylphenoxyacetic acid, 2-(4-chloro-2-methylphenoxy)propionic acid, 4-(4-chloro-2-methylphenoxy)butyric acid, 2-[4-(2', 4',-dichlorophenoxy)phenoxy]propanoic acid, 2,2-dichloropropionic acid , 7-oxabicyclo[2.2.1]heptane-2,3-dicarboxylic acid, (2,3,6-trichlorophenyl)acetic acid, glufosinate, [gallic acid, gibberellic acid, 3-indoleacetic acid, indole-3-butyric acid, 1-naphthaleneacetic acid, β-naphthoxyacetic acid,] N-(phosphonomethyl)glycine, 4-amino-3,5,6-trichloropicolinic acid, 3,5,6-trichloro-2-pyridinyloxyacetic acid, 9-undecylenic acid, and combinations thereof.

13. The method of claim 1 wherein the first neutralizing base is selected from group consisting of ammonia, dimethylamine, potassium hydroxide, ethylamine, ammonia, sodium hydroxide, sodium carbonate, potassium carbonate, sodium bicarbonate, potassium bicarbonate, isopropylamine, diethanolamine, trimethylamine, ethanolamine, and combinations thereof.

14. The method of claim 1, wherein the herbicidal salt composition is a powder having a range of particle size diameters of about 25 microns to about 5000 microns.

15. The method of claim 1, wherein the water-soluble herbicidal salt composition consists essentially of:
(a) about 95% to about 99.5% by weight of a dimethylammonium salt, a potassium salt or a diethanolamine salt, or mixtures, of an herbicidal compound selected from the group consisting of 2,4-dichlorophenoxyacetic acid, bentazon, 2,4-dichlorophenoxybutyric acid, 4-chloro-2-methylphenoxyacetic acid, 2 (4-chloro-2-methylphenoxy)propionic acid, N-(phosphonomethyl)glycine, 4 (4-chloro-2-methylphenoxy)butyric acid, 7-oxabicyclo[2.2.1-]heptane-2,3-dicarboxylic acid, 2-(2,4-dichlorophenoxy)propionic acid, and combinations thereof; and
(b) about 0.5% to about 3% by weight water, wherein an aqueous solution of the herbicidal salt composition is essentially free of insoluble matter and exhibits a pH in the range of about 5 to about 7.

* * * * *

UNITED STATES PATENT AND TRADEMARK OFFICE
CERTIFICATE OF CORRECTION

PATENT NO. : 5,266,553
DATED : November 30, 1993
INVENTOR(S) : Champion et al.

It is certified that error appears in the above-indentified patent and that said Letters Patent is hereby corrected as shown below:

Col. 4, line 59, delete "no" and insert -- not --.

Col. 10, line 31, after "2" delete "." and insert -- - --.

Col. 10, line 58, after "3" insert -- - --.

Col. 11, line 50, after "Equation" insert -- 1 --.

Col. 26, line 48, Claim 10 after "is" insert -- selected --.

Signed and Sealed this

Fourteenth Day of June, 1994

Attest:

BRUCE LEHMAN

*Attesting Officer*  *Commissioner of Patents and Trademarks*